(12) United States Patent
Kumar et al.

(10) Patent No.: US 10,317,325 B2
(45) Date of Patent: Jun. 11, 2019

(54) PREDICTION OF KINEMATIC VISCOSITY OF VACUUM RESIDUE AND REFINERY HEAVY PRODUCT BLENDS

(71) Applicants: Rajeev Kumar, Maharashtra (IN); Sonal Maheshwari, Maharashtra (IN); Ravi Kumar Voolapalli, Maharashtra (IN); Tushar Sudhakar Thorat, Maharashtra (IN); Sanjay Bhargava, Maharashtra (IN)

(72) Inventors: Rajeev Kumar, Maharashtra (IN); Sonal Maheshwari, Maharashtra (IN); Ravi Kumar Voolapalli, Maharashtra (IN); Tushar Sudhakar Thorat, Maharashtra (IN); Sanjay Bhargava, Maharashtra (IN)

(73) Assignee: Bharat Petroleum Corporation Limited, Mumbai, Maharashtra (IN)

( * ) Notice: Subject to any disclaimer, the term of this patent is extended or adjusted under 35 U.S.C. 154(b) by 226 days.

(21) Appl. No.: 15/272,237

(22) Filed: Sep. 21, 2016

(65) Prior Publication Data

US 2017/0322131 A1    Nov. 9, 2017

(30) Foreign Application Priority Data

May 3, 2016    (IN) .............................. 201621015432

(51) Int. Cl.
*G01N 11/00*    (2006.01)
*C10G 7/06*    (2006.01)
*G01N 33/28*    (2006.01)

(52) U.S. Cl.
CPC .............. *G01N 11/00* (2013.01); *C10G 7/06* (2013.01); *G01N 33/2823* (2013.01); *G01N 2011/0013* (2013.01); *G01N 2011/0093* (2013.01)

(58) Field of Classification Search
CPC ... G01N 11/00; G01N 2011/0093; C10G 7/06
See application file for complete search history.

(56) References Cited

U.S. PATENT DOCUMENTS

| | | | | |
|---|---|---|---|---|
| 5,452,601 A | * | 9/1995 | Hori | ........................ G01N 11/00 374/15 |
| 2012/0006289 A1 | * | 1/2012 | Petz | ........................ F01L 9/025 123/90.12 |

(Continued)

FOREIGN PATENT DOCUMENTS

WO    WO 2013/102916 A1    7/2013

OTHER PUBLICATIONS

Sattarin, M. et al, New Viscosity Correlation for Dead Crude Oils, Petroleum & Coal 49 (2) ISSN 1335-3055, Jun. 12, 2007, pp. 33-39.

(Continued)

*Primary Examiner* — Stephanie E Bloss
(74) *Attorney, Agent, or Firm* — Reinhart Boerner Van Deuren P.C.

(57) ABSTRACT

Provided is a method for predicting kinematic viscosity of a fraction of a crude oil to optimize selection of crude oils. The method includes receiving parameters of the crude oil, such as Vacuum Residue yield and Conradson Carbon Residue (CCR), content as an input. The method also includes determining kinematic viscosity of the fraction of the crude oil at a first predetermined temperature based on a first correlation model between the physical parameters of the crude oil and the kinematic viscosity at the first predetermined temperature. The method further includes generating the kinematic viscosity of the fraction of the crude oil at the predetermined temperature based on the first correlation model corresponding to the input. Also provided is a system for predicting kinematic viscosity at a predetermined temperature to optimize crude oil selection. Further provided is (Continued)

a method for estimating an amount of cutter stock for crude oil processing.

18 Claims, 11 Drawing Sheets

(56) References Cited

U.S. PATENT DOCUMENTS

| | | | | |
|---|---|---|---|---|
| 2014/0156241 | A1* | 6/2014 | Kumar | G01N 33/2823 |
| | | | | 703/6 |
| 2014/0180650 | A1* | 6/2014 | Kriz | G06F 17/5009 |
| | | | | 703/2 |
| 2015/0191598 | A1* | 7/2015 | Sirota | C08L 95/00 |
| | | | | 106/273.1 |
| 2015/0219541 | A1* | 8/2015 | Estrada | G01N 29/02 |
| | | | | 73/54.41 |
| 2017/0283711 | A1* | 10/2017 | Chen | B01D 3/10 |

OTHER PUBLICATIONS

Abu-Eishah S. I., A New Correlation for Prediction of the Kinematic Viscosity of Crude Oil Fractions as a Function of Temperature, API Gravity, and 50% Boiling-Point Temperature, International Journal of Thermophysics vol. 20, No. 5, Sep. 1999, pp. 1425-1434, Plenum Publishing Corporation.

* cited by examiner

US 10,317,325 B2

PREDICTION OF KINEMATIC VISCOSITY OF VACUUM RESIDUE AND REFINERY HEAVY PRODUCT BLENDS

CROSS-REFERENCE TO RELATED PATENT APPLICATION

This patent application claims priority to Indian Application No. 201621015432, filed May 3, 2016, the entire teachings and disclosure of which are incorporated herein by reference thereto.

FIELD OF INVENTION

The present invention relates to predicting kinematic viscosity of a fraction of a crude oil and, in particular, relates to predicting kinematic viscosity of vacuum residue and refinery heavy product blends based on physical parameters of the crude oil.

BACKGROUND

Crude oil is a naturally occurring, unrefined petroleum product comprising mixture of hydrocarbons and other organic material, extracted from natural underground reservoirs. Crude oils are processed and refined at petroleum refineries to produce commercially applicable refinery products, such as liquefied petroleum gas, gasoline, kerosene, diesel, etc.

Generally, a number of crude oils are selected by refineries for making commercially applicable refinery products. Crude oils are of many types which come from different sources around the world. The decision as to what crude oil or combination of crude oil to process depends on many factors including quality, availability, volume, demand, product specifications, and price. Further, the amounts and properties of the refinery products that can be obtained from each crude oil is also an important factor. Selection of crude oils is, therefore, a key part of refining process.

The refining process begins as a simple distillation of crude oil, which yields different refinery products and byproducts like residues, at different temperatures. The residues may be subjected to different processes that may involve addition of cutter stock for ease of processing of the residues. The addition of cutter stock in such processes may incur more expenses, change properties of refinery products, and/or impact the quality of the commercial products produced. Therefore, the amount of cutter stock used could impact the economics of refining processes and influence crude oil selection.

BRIEF SUMMARY OF THE INVENTION

In one aspect, embodiments of a method for predicting kinematic viscosity of a fraction of a crude oil to optimize selection of crude oils is provided. The method includes the step of receiving, by a processor, physical parameters of the crude oil as an input, wherein the physical parameters comprise at least one of Vacuum Residue yield and Conradson Carbon Residue (CCR) content. The method also includes the step of determining, by the processor, kinematic viscosity of the fraction of the crude oil at a first predetermined temperature, wherein the kinematic viscosity is determined based on a first correlation model between the physical parameters of the crude oil and the kinematic viscosity at the first predetermined temperature. Additionally, the method includes the step of generating an output based on the first correlation model corresponding to the input, wherein the output is the kinematic viscosity of the fraction of the crude oil at the predetermined temperature.

In embodiments of the method, the method can further include determining the kinematic viscosity of a heavy product blend from the kinematic viscosity of fraction of the heavy product blend based on a second correlation model. In such embodiments, the heavy product blend may correspond to a blend of different fractions of the crude oil derived from different or same crude oils.

In other embodiments, the method may further include determining kinematic viscosity of the fraction at a second predetermined temperature from kinematic viscosity of the fraction of crude oil at the predetermined temperature based on a third correlation model.

In still other embodiments, the fraction of the crude oil can be Vacuum Residue of the crude oil.

In yet further embodiments, the physical parameters may include one or more of API gravity, Sulphur content, Hydrogen content, Nitrogen content, Mercaptan value, Pour point, Saturates, Aromatics, Resins and Asphaltenes.

Moreover, in embodiments, the kinematic viscosity of the fraction of crude oil generated determines production requirements of Fuel oil, Low Sulphur Heavy Stock, Low Sulphur Fuel Oil, and bitumen.

Furthermore, in embodiments, the predetermined temperature can be in a range of 50 degree Celsius to 135 degree Celsius.

In another aspect, a system for predicting kinematic viscosity at a predetermined temperature to optimize crude oil selection is provided. The system includes a processor; a database comprising crude oil data, wherein the crude oil data comprises physical parameters of a crude oil; and a memory coupled to the processor and the database. The memory is programmed to include a first prediction module to predict kinematic viscosity of a fraction of the crude oil from the physical parameters of the crude oil. The physical parameters of the crude oil include at least one of vacuum residue yield and Conradson Carbon Residue (CCR) content. The memory is also programmed to include a second prediction module to predict the kinematic viscosity of a heavy product blend from the kinematic viscosity of fractions of the heavy product blend.

In embodiments of the system, the memory may also include a third prediction module to predict kinematic viscosity of fraction of crude oil at a second predetermined temperature from kinematic viscosity of the fraction at the predetermined temperature.

In another embodiment of the system, the predetermined temperature may be in a range of 50 degree Celsius to 135 degree Celsius.

In still another embodiment of the system, the memory may further comprise a fourth prediction module to predict the amount of optimal cutter stock requirement for evacuating vacuum residue.

In yet another embodiment of the system, the physical properties can include one or more of API gravity, Sulphur content, Hydrogen content, Nitrogen content, Mercaptan value, Pour point, Saturates, Aromatics, Resins and Asphaltenes.

Further, in the system, the heavy product blend can be obtained by blending different fractions of the crude oils derived from different or same crude oils.

In still another aspect, a method for estimating an amount of cutter stock for crude oil processing is provided. The method includes the steps of determining, by a processor, kinematic viscosity of vacuum residue of a crude oil based on physical parameters of the crude oil, wherein the physical parameters comprise at least one of Vacuum Residue yield and Conradson Carbon Residue (CCR) content, and calculating, by the processor, the amount of cutter stock based on the kinematic viscosity of vacuum residue of the crude oil.

In embodiments of the method, the cutter stock can be a blend of one or more fractions of the crude oil.

In other embodiments of the method, the cutter stock can include one or more of kerosene, gasoline, jet fuel, diesel, Naphtha, VGO, CLO, LCO, LSHS, FO, LSFO, and VR.

In still other embodiments of the method, the amount of cutter stock can be calculated as a weight percentage of a refinery product.

Further, in embodiment of the method, the crude oil processing can include optimal evacuation of vacuum residue from a vacuum distillation column.

Moreover, in embodiments of the method, the physical parameters can include one or more of API gravity, Sulphur content, Hydrogen content, Nitrogen content, Mercaptan value, Pour point, Saturates, Aromatics, Resins and Asphaltenes.

BRIEF DESCRIPTION OF DRAWINGS

The detailed description is provided with reference to the accompanying figures. In the figures, the left-most digit(s) of a reference number identifies the figure in which the reference number first appears. The same numbers are used throughout the drawings to reference like features and components.

DETAILED DESCRIPTION

Figure 1:
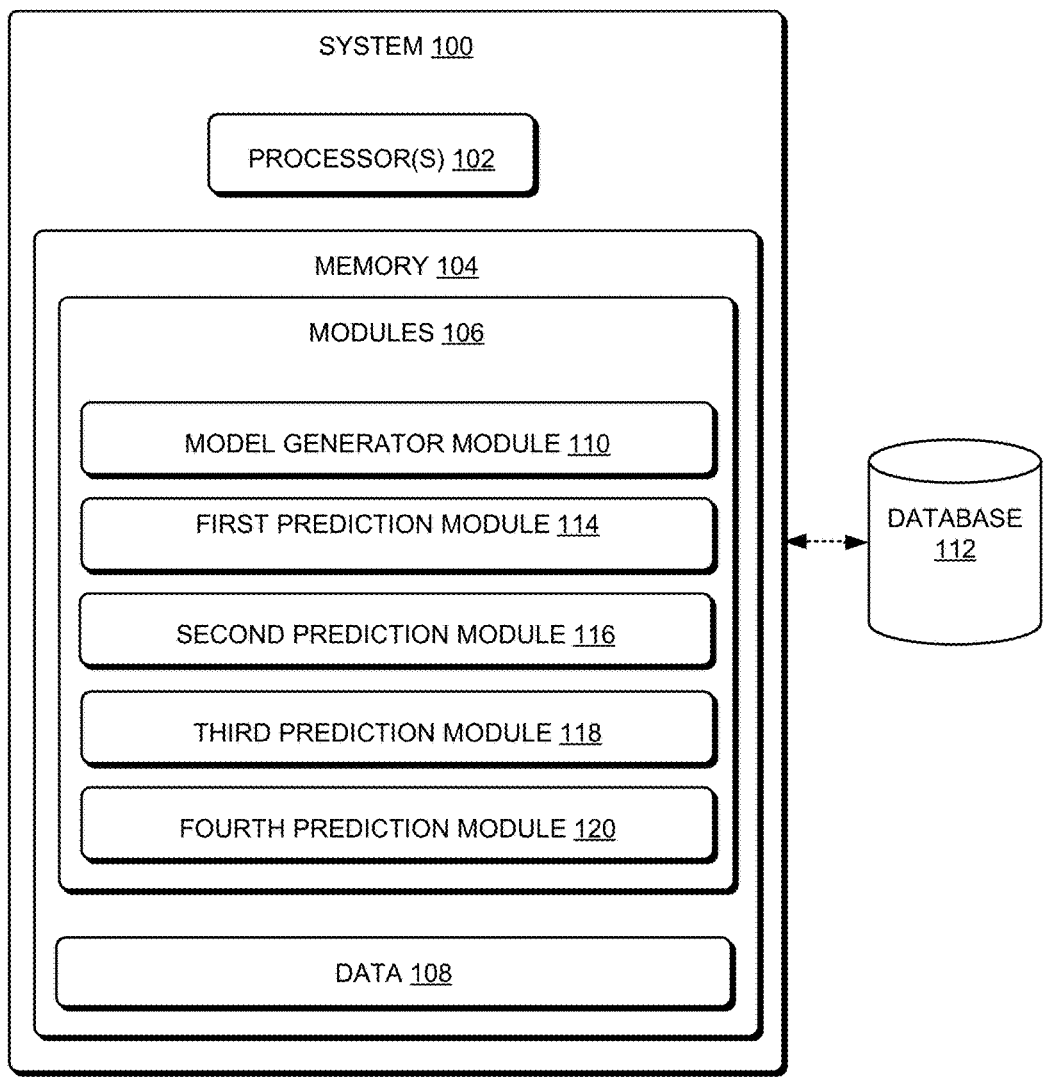
FIG. 1 illustrates a system for predicting kinematic viscosity, in accordance with an implementation of the present subject matter.

The present subject matter, relates to methods and systems for predicting the kinematic viscosity of a fraction of crude oil at a predetermined temperature based on physical parameters of the crude oil. While the following description encompasses prediction of kinematic viscosity of vacuum residue at 50, 100, and 135 degree Celsius as an example, it will be understood that prediction of kinematic viscosity of other fractions of crude oil at other temperatures may also be performed, as would be evident to a person skilled in the art.

There are various varieties of crude oils that are available in the petroleum market, of which Kuwaity crude oil, Bombay High crude, Arab Light crude, and Saharan Blend Crude oil are prominent examples. Generally, different crude oils are selected by petroleum refineries to produce refinery products. Each crude oil has different composition of fractions and different properties. These crude oils are blended and subsequently subjected to refining processes for the separation of different hydrocarbons present in the crude oil into useful petroleum fractions.

Generally, the petroleum refining process involves atmospheric distillation and vacuum distillation of crude oils. In these processes, a crude oil or a blend of crude oils is separated into fractions on the basis of the boiling points of each fraction. Hence, yield of different fractions is obtained at different temperatures. In atmospheric distillation column, lighter fractions, such as Liquefied Petroleum Gas (LPG), Naphtha, Light Kerosene (LK), Heavy Kerosene (HK), Light Gas Oil (LGO), Heavy Gas Oil (HGO), etc., are separated or fractionated owing to their relatively low boiling points. The heavier fractions having high boiling points are transferred to a vacuum distillation column. Distillation under vacuum permits fractionation at lower temperature and fractions, such as Vacuum Diesel (VD), Light vacuum gas oil (LGO), Heavy vacuum gas oil (HGO), etc., can be obtained, while remaining fractions settle in the bottom of the column as vacuum residue (VR).

Vacuum residue is a fraction of the crude oil having boiling point generally above 500 degree Celsius and is obtained at the bottom of vacuum distillation column. The vacuum residue is sent to intermediate storage or is typically processed further in residue upgradation facilities. In the absence of residue upgradation facilities, vacuum residues are subjected to an evacuation process to yield fuel oils (FO), low sulphur heavy stock (LSHS) and low sulphur fuel oil (LSFO) that may further be used as a refinery heavy product blends. The refinery heavy product blends obtained from the vacuum residue may also be used to blend with other refinery products to produce commercially applicable refinery products.

In the evacuation of vacuum residue, cutter stocks are added to the vacuum residue to reduce the kinematic viscosity of vacuum residue. Cutter stocks or distillate liquids are petroleum products which reduce the viscosity of heavier petroleum stocks by dilution. Naphtha, Kerosene, Gas Oils, Vacuum Gas Oil (VGO), Clarified Oil (CLO), Light Cycle Oil (LCO), Low Sulphur Heavy Stock (LSHS), Fuel oil (FO), Low Sulphur Fuel Oil (LSFO), etc., are common examples of cutter stocks. The amount of cutter stock to be combined with vacuum residue in this process is an important decision taken at petroleum refineries and is based on various parameters, which includes an estimated kinematic viscosity of the residue to be processed. An inaccurate amount of cutter stock used influences the quality of the refinery product and crude oil selection for overall refinery profitability. Further, an excess amount of cutter stock would not only lead to wastage of cutter stock but also incur additional expenses associated with it. Therefore, better estimations of amount of cutter requirement help to minimize the quality giveaways in crude oil processing.

Typically, refiners estimate the amount of cutter stock to be added based on flow properties like kinematic viscosity of the vacuum residue of crude oils provided by the suppliers of the crude oil. Since vacuum residue does not flow at room temperature due to high pour point, an experimental measurement of kinematic viscosity is not possible. The kinematic viscosity of vacuum residue is estimated theoretically by the suppliers, based on which cutter stocks are added by the refiners. However, the kinematic viscosity of vacuum residue at 50 degree Celsius, provided by the suppliers is sometimes observed to be extremely high. For example, kinematic viscosity of vacuum residue of Kuwaity crude oil at 50 degree Celsius is predicted by suppliers to be in the range of 6.24E+08 from crude oil assay analysis. These predicted values are being used for 180cSt and 380cSt grades of Fuel Oil production which has been resulting in high cutter requirement and in turn, selection of Kuwaity crude and other similar low cost crude oils has become non-viable.

As mentioned above, prediction of properties of fractions of crude oils and refinery product blends affects the economics and selection of crude oils. An inaccurate estimate of properties of crude oil fraction may result in production of substandard refinery products and increase the cost involved.

In accordance with the present subject matter, a method and system for predicting kinematic viscosity of a fraction of crude oil at a predetermined temperature is described. For example, the method and system is used to predict the kinematic viscosity of vacuum residue based on the physical parameters of the crude oil. The method uses correlation models to predict the kinematic viscosity of vacuum residue accurately. In one implementation, the method also uses a correlation model to predict the kinematic viscosity of a heavy product blend using the kinematic viscosity of the fractions of the heavy product blend.

The method described herein, is based on the measurement of one or more physical parameters of the crude oil or crude oil blend. The one or more physical parameters includes at least one of Vacuum Residue yield and Conradson Carbon Residue (CCR) content of the crude oil or the crude oil blend. In one example, one or more of other physical parameters, such as API gravity, Nitrogen content, Sulphur content, Mercaptan value, Pour point, Saturates, Aromatics, Resins and Asphaltenes, etc., may also be used in combination with at least one of Vacuum Residue yield and Conradson Carbon Residue (CCR) content for prediction of kinematic viscosity.

The physical parameters of the crude oil can be measured by different techniques as will be understood. For example, crude oil samples can be subjected to TBP and Pot Still distillations based on ASTM D2892 and D5236 respectively to generate sufficient vacuum residue samples. Similarly, other industrial methods, such as ASTM D2622, D4294, and D5453 can be used to measure sulphur content of the crude oils. The nitrogen content of crude oil can be measured by ASTM D4629. Further, the Conradson Carbon Residue (CCR) content of the crude oil is measured by ASTM D189 and API gravity is measured by ASTM D4052. Kinematic viscosity of vacuum residue have been measured based on ASTM D2170. In some cases, such as at lower temperatures, it may not be possible to determine the kinematic viscosity of vacuum residue experimentally using the ASTM method as the sample may not flow. In such cases, the kinematic viscosity may be determined by adding cutter stock to vacuum residue samples and extrapolating the results, as will be discussed later.

As discussed above, the physical parameters are measured for various types of crude oils and are later used for regression analysis. For this, the values of the physical parameters measured may be stored in a database, referred to as crude oil database. Based on the values of the physical parameters, regression analysis is performed against the kinematic viscosities measured or extrapolated, as required, to obtain coefficients of regression that can be used for prediction of kinematic viscosity of vacuum residue.

In one implementation, a first correlation model is developed based on the coefficients obtained by regression analysis between the physical parameters of the crude oil and the kinematic viscosity of vacuum residue at the predetermined temperature. The predetermined temperature is in a range of 50 degree Celsius to 135 degree Celsius.

In one implementation, a second correlation model and third correlation model may be developed based on coefficients obtained by experimental analyses. For example, the second correlation model may be used to predict kinematic viscosity of a blended petroleum product including a heavy product, from the kinematic viscosities of individual products in the blended petroleum product. Further, the third correlation model may be used to predict kinematic viscosity of vacuum residue of crude oil at a first predetermined temperature from the kinematic viscosity of vacuum residue of the crude oil at a second predetermined temperature. The experimental analyses may involve analyzing behavior of properties of crude oils and crude oil blends, as will be discussed later.

The correlation models can be used to determine the kinematic viscosity of vacuum residue of any given crude oil, or blend of crude oils. The physical parameters of the given crude oil may be used as an input to the correlation model. Using the inputs, the correlation model determines the kinematic viscosity of the vacuum residue of the given crude oil as output.

In another embodiment of the present subject matter, the prediction of kinematic viscosity of vacuum residue of crude oil can be used to estimate the amount of cutter stock to be used in processing of the vacuum residue. Cutter stocks reduce the viscosity of vacuum residue by dilution and the vacuum residue is evacuated as Fuel Oils (FO), Low Sulphur Heavy Stock (LSHS), and Low Sulphur Fuel Oil (LSFO) upon processing. The amount of cutter stock to be used depends on the type of cutter stock selected and varies proportionally with the kinematic viscosity of vacuum residue.

The prediction of kinematic viscosity of vacuum residue of crude oil based on the methods of the present subject matter is simple, less time consuming, and more accurate in comparison to existing methods. Further, the prediction of kinematic viscosity of vacuum residue using physical parameters of crude oil including at least one of Vacuum residue yield and Conradson Carbon Residue (CCR) content enables accurate estimation of cutter stocks in crude oil processing, which helps in selecting crude oils appropriately, minimizing cutter usage, and maximizing refinery profits.

FIG. 1 illustrates a schematic diagram of a system 100 for predicting kinematic viscosity at a predetermined temperature, according to an embodiment of the present subject matter. The system comprises one or more processor(s) 102 and a memory 104, coupled to the processor 102. It will be understood that the system 100 may be implemented as any computing system known in the art, such as a desktop, a laptop, server, etc.

The processor 102 may contain one or more processing units, which are configured to receive and execute computer-readable instructions and data stored by the memory 104. The processor 102 may be implemented as a microprocessor, microcontroller, central processing unit, and the like.

The memory 104 may include any computer-readable medium known in the art including, volatile memory, such as static random access memory (SRAM) and dynamic random access memory (DRAM), and/or non-volatile memory, such as read only memory (ROM), hard disks, optical disks, magnetic tapes, etc. Further, the memory 104 includes module(s) 106 and data 108. The modules 106 may include routines, programs, objects, components, data structures, etc., which perform specific functions.

The data 108 is capable of storing data processed, received, and generated by one or more of the modules 106. The modules 106 may further include a model generator module 110, and a plurality of prediction modules. Correlation models are generated by the model generator module 110 and the predicted values are generated by the plurality of prediction modules. The data 108 includes data generated as a result of the execution of one or more modules.

The system 100 as illustrated in FIG. 1 predicts kinematic viscosity by generating a correlation model based on coefficients generated from a regression analysis. The model generator module 110 receives values for physical parameters of crude oils from the crude oil database 112. The physical parameters include at least one of Vacuum Residue yield and Conradson Carbon Residue (CCR) content for a plurality of known crude oils. In one implementation, the physical parameters may also include one or more of API gravity, Sulphur content, Hydrogen content, Nitrogen content, Pourpoint, Viscosity, Saturates, Aromatics, Resins, Asphaltenes in combination with at least one of Vacuum Residue yield and Conradson Carbon Residue (CCR) content.

The physical parameters are measured using various industrial protocol methods. Table. 1 depicts a list of physical parameters and the measurement methods used for each physical parameter.

TABLE 1

Industrial Methods for measurement of Physical properties.

| Sample | Analyses Details | Method |
|---|---|---|
| Any given oil sample | Density, Specific Gravity and/or API Gravity | ASTM D4052 |
| | Sulphur | ASTM D2622, D4294, D5453 |
| | Mercaptan | ASTM D3227 |
| | Kinematic Viscosity (KV) | ASTM D445 |
| | Pour Point | ASTM D97, D5853, D5950 |
| | Acidity | ASTM D664 |
| | Fe, V, Ni, Na, Cu, Zn | ICP-AES |
| | Total Nitrogen | ASTM D4629 |
| | Basic Nitrogen | UOP 269 |
| | Yields (% wt & % vol) | ASTM D2892 and D5236 |
| | ASTM Distillation | ASTM D86 |
| | Freezing Point | ASTM D2386 |
| | Conradson Carbon Residue (CCR) | ASTM D189 |
| | Micro Carbon Residue (MCR) | ASTM D4530 |
| | Ramsbottom Carbon Residue (RCR) | ASTM D524 |
| | Asphaltenes | ASTM D6560 |
| | Salt | ASTM D3230 |
| | RVP | ASTM D323 |

As depicted above in Table 1, industrial protocol methods for measurement of physical parameters of crude oils and their fractions are known. In some cases, such as at lower temperatures, it may not be possible to determine the kinematic viscosity of vacuum residue experimentally using the ASTM method as the sample may not flow. In such cases, the kinematic viscosity may be determined by adding cutter stock to vacuum residue samples and extrapolating the results, as will be discussed later.

The crude oil database 112 stores the values for physical parameters of crude oils and its fractions as data. This data is then used by the model generator module 110 for calculating coefficients based on which correlation models are generated. In one implementation, the model generator module 110 calculates the regression coefficients based on a combination of linear and non-linear regressions. It may be noted that, these measured physical properties include at least VR yield and Conradson Carbon Residue (CCR) content. Additionally, one or more physical properties selected from the group of API gravity, Sulphur content, Hydrogen content, Nitrogen content, Mercaptan value, Kinematic viscosity, Pour point, Saturates, Aromatics, Resins, and Asphaltenes can be used. It will be understood that other methods of non-linear regression may also be used for determination of the regression coefficients.

Further, the plurality of prediction modules includes a first prediction module 114 and a second prediction module 116. The first prediction module 114 and the second prediction module 116 can predict kinematic viscosity based on the correlation models generated by the model generator module 110. The first prediction module 114 predicts kinematic viscosity of vacuum residue at a predetermined temperature of given crude oil. Similarly, the second prediction module 116 predicts the kinematic viscosity of refinery heavy product blends. In one implementation, a third prediction module 118 is used for prediction of kinematic viscosity of vacuum residue at a first predetermined temperature from kinematic viscosity of vacuum residue at a second predetermined temperature for a given crude oil. The values of predicted kinematic viscosity generated by plurality of prediction modules may subsequently be stored in data 108 for further calculations.

In another embodiment of the present subject matter, the plurality of modules includes a fourth prediction module 120. The fourth prediction module 120 predicts an amount of cutter stock to be used for processing the vacuum residue having the predicted kinematic viscosity. Cutter stocks or cutter liquids refer to petroleum products which reduce viscosity of heavier crude oil including residues, by dilution. The vacuum residue is evacuated as a fuel oil on addition of cutter stock. The fourth prediction module 120 calculates amount of cutter stock required as a weight percentage of the fuel oil produced. The calculation is based on the values of predicted kinematic viscosity stored in data 108.

Figure 2:
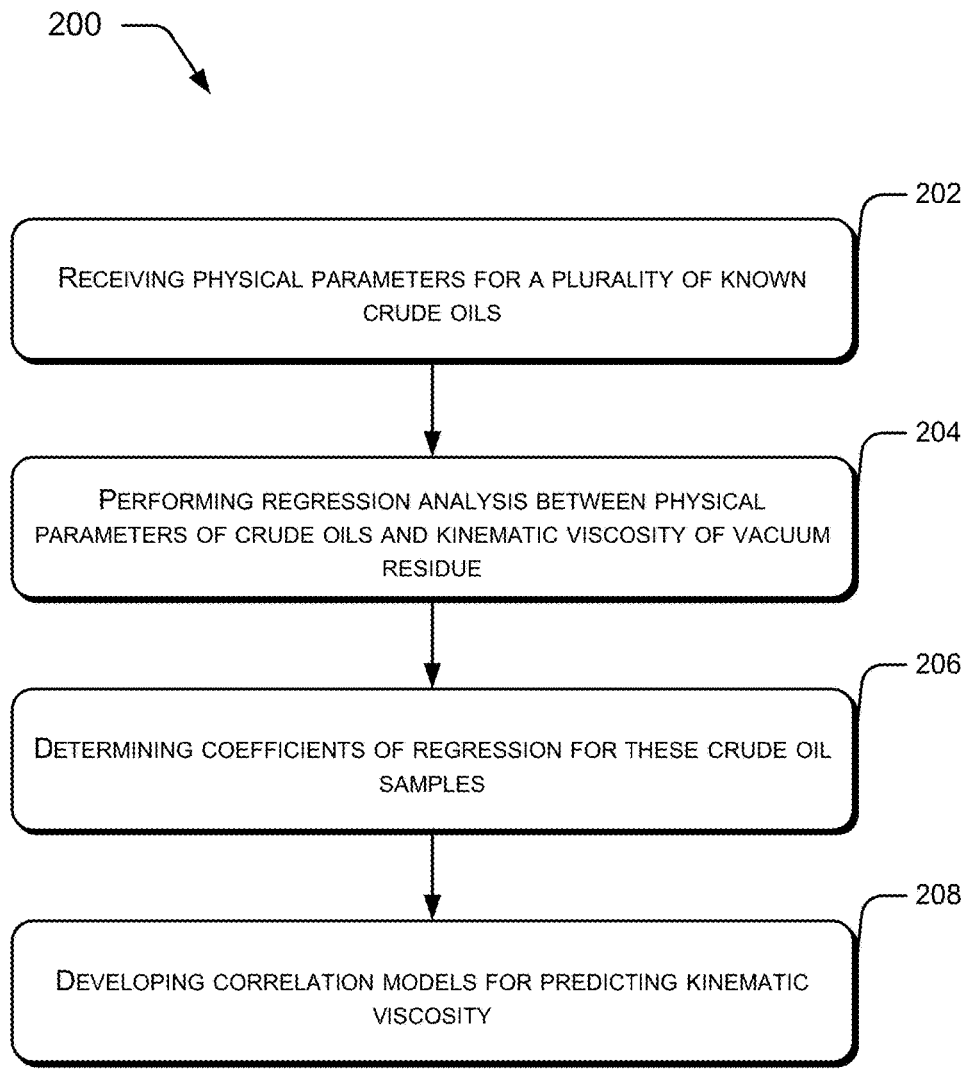
FIG. 2 illustrates a method for developing a correlation model for predicting kinematic viscosity, in accordance with an implementation of the present subj ect matter.

FIG. 2 illustrates a method 200 for developing correlation models for predicting kinematic viscosity. The method 200 described with reference to the system 100 described earlier, however, it will be understood that the method 200 can be implemented in other systems also.

At block 202, values of physical parameters of plurality of known crude oils and the kinematic viscosity of vacuum residue at a predetermined temperature are received from the crude oil database 112. For example, the model generator module 110 may receive values of physical parameters measured using various techniques. The physical parameters include at least one of Vacuum Residue yield and Conradson Carbon Residue (CCR) content. It may also receive one or more of other physical parameters including API gravity, Sulphur content, Nitrogen content, Hydrogen content, Saturates content, Aromatics content, etc.

At block 204, the model generator module 110 performs regression analysis between the measured physical parameters of crude oils and kinematic viscosity of vacuum residue at a predetermined temperature.

At block 206, coefficients of regression are determined based on the regression analysis between measured physical parameters of a crude oil and kinematic viscosity of vacuum residue at a predetermined temperature. The coefficients of regression may be calculated based on linear regression or non-linear regression.

At block 208, the model generator module 110 develops correlation models for prediction of kinematic viscosity. The correlation models are developed based on the coefficients of regression obtained through regression analysis. In one implementation, the correlation models may be developed based on coefficients calculated from experiments.

In one implementation, a first correlation model is developed by the model generator module 110 based on the coefficients of regression calculated. The first correlation model predicts the kinematic viscosity of vacuum residue of a crude oil at a predetermined temperature from the physical parameters of the crude oil. Theoretically, the first correlation model may be written as, KV-VR @ 50, 100, or 135 degree Celsius=f (at least one of Vacuum Residue yield and Conradson Carbon Residue (CCR) content)

where,

KV-VR denotes kinematic viscosity of vacuum residue of crude oil.

In one example, the first correlation model may be

KV-VR @ 50, 100, or 135 degree Celsius=f (Vacuum Residue yield, CCR content, and API gravity)

In another example, other combinations of physical parameters may be used with at least one of Vacuum residue yield and Conradson Carbon Residue (CCR) content.

In another implementation, a second correlation model developed by the model generator module 110 based on experimental analysis, predicts the kinematic viscosity of refinery heavy product blends from kinematic viscosity of fractions of crude oils derived from different or same crude oils individual crude oils or streams can be taken from other refinery processing units.

Theoretically, the second correlation model may be written as

Viscosity Index (VI)=$(LOG_{10}(LOG_{10}(KV$ at 50° C.)+ 0.43324))

Viscosity Blending Number (VBN)=$\Sigma\ X_iVI_i$

KV, cSt at 50° C.=$10^{\wedge}(10^{\wedge}((VBN))-0.43324)$ where,

KV denotes kinematic viscosity of a crude oil, $X_i$ denotes fraction of crude oil in the crude oil blend, $VI_i$ denotes viscosity index of the crude oil, cSt denotes centistokes (CGS unit of kinematic viscosity).

In above implementation, the second correlation model may have a coefficient ranging from 0.2 to 0.9.

In yet another implementation, a third correlation model developed by the model generator module 110 based on experimental analysis, predicts the kinematic viscosity of vacuum residue of crude oil at first predetermined temperature from the kinematic viscosity of vacuum residue of crude oil at second predetermined temperature.

Theoretically, the third correlation may be written as,

KV-VR @ 50° C.=$10^{\wedge}(10^{\wedge}(0.98750*((\log_{10}(\log_{10}(KV@100°\ C.))))))+0.2002$ where, KV-VR denotes kinematic viscosity of vacuum residue of crude oil.

In above implementation, the third correlation model may have a coefficient ranging from 0.7 to 0.9999. Similarly, kinematic viscosity of vacuum residue at 50 degree Celsius can also be predicted from kinematic viscosity of vacuum residue at 135 degree Celsius.

Further, the order in which the method blocks are described is not intended to be construed as a limitation, and any number of the described method blocks can be combined in any order to implement the method, or an alternative method. Additionally, individual blocks may be deleted from the methods without departing from the scope of the subject matter described herein. Furthermore, the methods can be implemented in any suitable hardware, software, firmware, or combination thereof.

Figure 3:
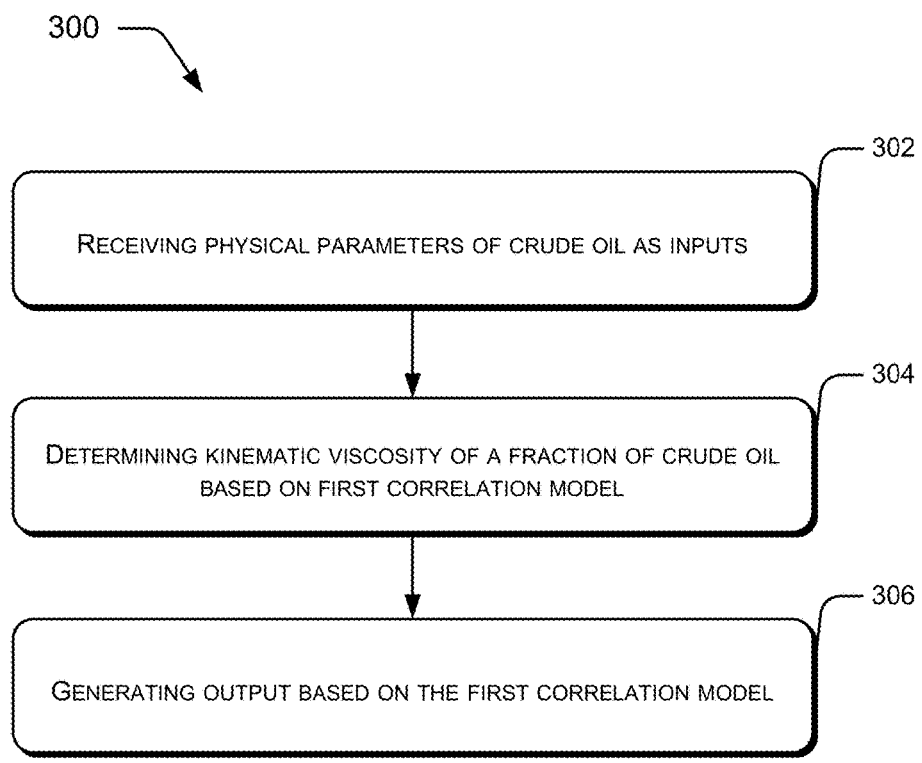
FIG. 3 illustrates a method for predicting kinematic viscosity from physical parameters of crude oil based on a first correlation model, in accordance with an implementation of the present subject matter.

FIG. 3 illustrates a method 300 for predicting kinematic viscosity of vacuum residue from crude oil parameters. The method 300 described with reference to the system 100 described earlier, however, it will be understood that the method can be implemented in other systems also.

At block 302, values of physical parameters, including at least one of Vacuum Residue yield and Conradson Carbon Residue (CCR) content of crude oil are received as inputs to the first correlation model from the data. The data may include values of physical parameters of crude oils whose kinematic viscosity of vacuum residue is unknown. In one implementation, the values of physical parameters may be provided by a user through one or more interfaces. The interfaces may include peripheral devices, such as mouse, keyboard, external memory, etc. The first prediction module may access the data for receiving values of physical parameters as input. The physical parameters of the selected crude oil may also include one or more of API gravity, Sulphur content, Hydrogen content, Nitrogen content, Pour point, Saturates, Aromatics, Resins, Asphaltenes, etc. For example, the physical parameters include Vacuum Residue yield, Conradson Carbon Residue (CCR) content, and API gravity.

At block 304, the kinematic viscosity of vacuum residue of crude oil at a predetermined temperature is determined. The correlation model on receiving the values of physical parameters, calculates an estimated value of kinematic viscosity of vacuum residue of crude oil.

At block 306, the predicted value of kinematic viscosity is generated as an output based on the first correlation model. The output generated is a predicted value of kinematic viscosity of vacuum residue of crude oil. In one implementation, the predicted value of kinematic viscosity may be used for determining production requirements of Fuel oil, Low Sulphur Heavy Stock, Low Sulphur Fuel Oil, and bitumen, and estimating amount of cutter stock required in vacuum residue evacuation process.

Figure 4:
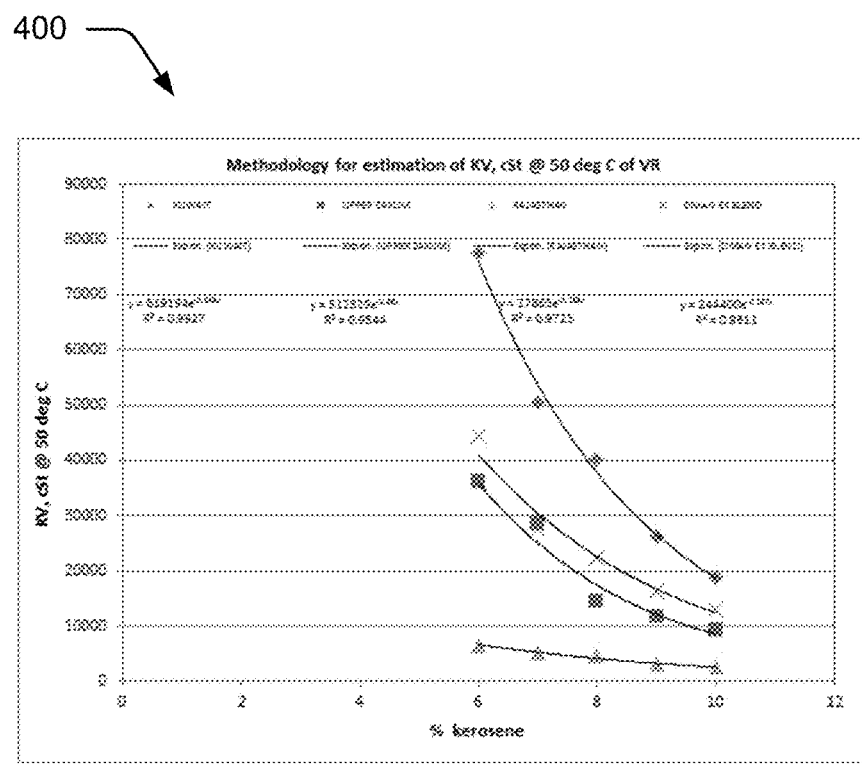
FIG. 4 illustrates relationship between cutter stock and kinematic viscosity of vacuum residue of given crude oil, in accordance with an implementation of the present subject matter.

FIG. 4 illustrates a regression analysis 400 between percentage of cutter stock and kinematic viscosity of vacuum residue of crude oil at 50 degree Celsius, based on an experimental investigation for extrapolating and determining kinematic viscosity of vacuum residue obtained from known crude oil samples. For the experimental investigation, kerosene is used as cutter stock. However, Naphtha, Gas Oils, vacuum gas oil (VGO), clarified oil (CLO), light cycle oil (LCO), Low Sulphur Heavy Stock (LSHS), Fuel oil (FO), Low Sulphur Fuel Oil (LSFO), gasoline, diesel, and the like may also be used as cutter stock for studying the relationship between kinematic viscosity and cutter.

Vacuum residue is a fraction of a crude oil having high boiling point in a range of more than 500 degree Celsius. At the end of vacuum distillation process, the vacuum residue accumulates at the bottom of the vacuum distillation column. The vacuum residue is evacuated from the vacuum residue column by adding cutter stocks. The cutter stocks reduce the resistance to flow of the vacuum residue by dilution and combine with the residue to produce refinery heavy product blends. Therefore, kinematic viscosity of vacuum residue of crude oil decreases with the addition of cutter stock. This relationship between vacuum residue and cutter stock is the basis for experimentally determining kinematic viscosity of vacuum residue of a crude oil at 50 degree Celsius using vacuum residue sample.

The experiment requires a set of sample crude oils and the vacuum residue of each sample crude oil. In an implementation, Kuwaity crude oil, Upper Zakum, Rajasthan crude oil, Oman ex blend, etc., may be used as samples of crude oils. The vacuum residues of each sample crude oil are subjected to different amounts of Kerosene and the kinematic viscosity of each sample is measured. The measurement of kinematic viscosity may be performed by using viscometers, kinematic viscometers, or by using industrial protocol methods, such as ASTM D2170.

On gathering and compiling the measurements of kinematic viscosity for different values of cutter, a methodology can be developed as depicted in FIG. 4. The figure represents a scatter plot between kinematic viscosity of blend of vacuum residue and kerosene at 50 degree Celsius and percentage of kerosene in vacuum residue. The experiment shows that at 50 degree Celsius, the kinematic viscosity of blend of vacuum residue and kerosene requires a minimum of 6% of cutter stock, below which the vacuum residue ceases to flow. The kinematic viscosity of vacuum residue of Kuwaity crude oil as derived from the graph can be written as, $$y = 619194 e^{-0.349x},$$

where,
y denotes the kinematic viscosity of vacuum residue, and
x represents the cutter stock %.

Mathematically, the value of kinematic viscosity of vacuum residue can be determined by limiting value of x to zero, therefore, $$y_{lim\ x->0} = 6.19E+05$$

The above equation represents the experimentally derived kinematic viscosity of vacuum residue of crude oil at 50 degree Celsius. This experimental value of kinematic viscosity may further be used for regression analysis for developing a correlation for predicting kinematic viscosity.

FIG. 5-FIG. 12 illustrate graphs depicting the influence of the physical parameters of crude oil on kinematic viscosity of vacuum residue of the crude oil at a predetermined temperature. It will be understood by a person skilled in the art that for different crude oils, similar influence of physical parameters on kinematic viscosity of vacuum residue may be observed. Based on the illustrated graphs, the parameters for developing the first correlation model may be determined as will be explained.

The graphs illustrated in the FIG. 5-FIG. 12 are generated by studying the relationship of physical parameters of crude oil and kinematic viscosity of vacuum residue at 100 degree Celsius. The temperature must not be construed as a limitation as a person skilled in the art would understand that similar influence of physical parameters on kinematic viscosity of vacuum residue may be observed in a temperature range of 50 to 135 degree Celsius.

The graphs depict the change in kinematic viscosity of vacuum residue due to change in physical parameters of the crude oil. The independent variables in the graphs (x-axis) represent the change in physical parameters of the crude oil and the dependent variable (y-axis) represents the change in kinematic viscosity of vacuum residue of the crude oil. Further, the graphs are derived purely for studying the impact caused on kinematic viscosity of vacuum residue due to physical parameters in terms of magnitude. Therefore, the dependent and independent variables represent merely the deviation in the values and not the increase or decrease of the parameter or property. In other words, the dependent variable Y represents $|\Delta y|$ and the independent variable X represents $|\Delta x|$.

Figure 5:
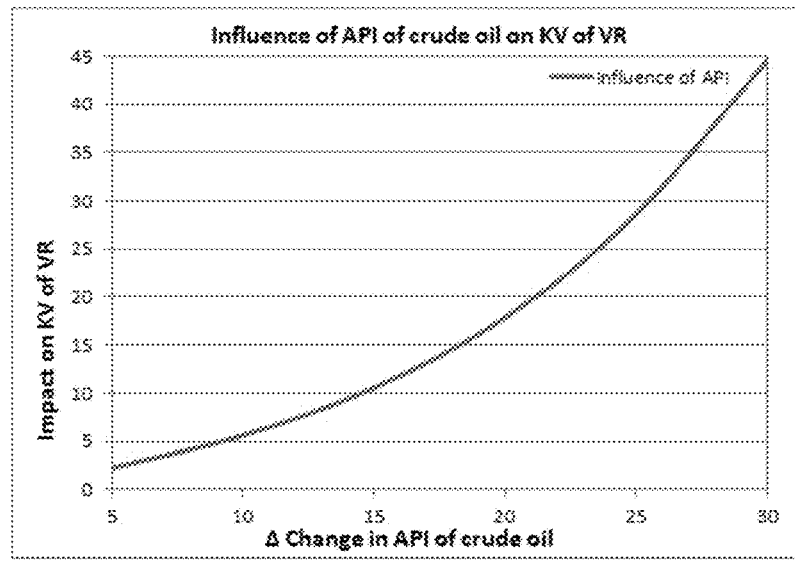
FIG. 5 illustrates impact on kinematic viscosity of vacuum residue of a crude oil due to change in API gravity of crude oil, in accordance with an implementation of the present subject matter.

FIG. 5 illustrates the impact of change in API gravity of crude oil on the kinematic viscosity of vacuum residue of the crude oil. The API gravity of crude oils may be measured using industrial protocol methods like ASTM D4052 or ASTM D1298. A change in the value of API gravity yields a change in the kinematic viscosity of vacuum residue, as shown in the figure.

For the given crude oil, the change in API gravity may be varied up to 30 units. However, the change in API gravity of a typical crude oil can be varied from 10-60 units. The relationship between the change in API gravity and change in kinematic viscosity is non-linear. For a given crude oil, a change of 5 units of API gravity shows a noticeable change in the kinematic viscosity of vacuum residue. Further, overall, there is a change of 45 units of kinematic viscosity of vacuum residue due to a change in 30 units of API gravity.

Figure 6:
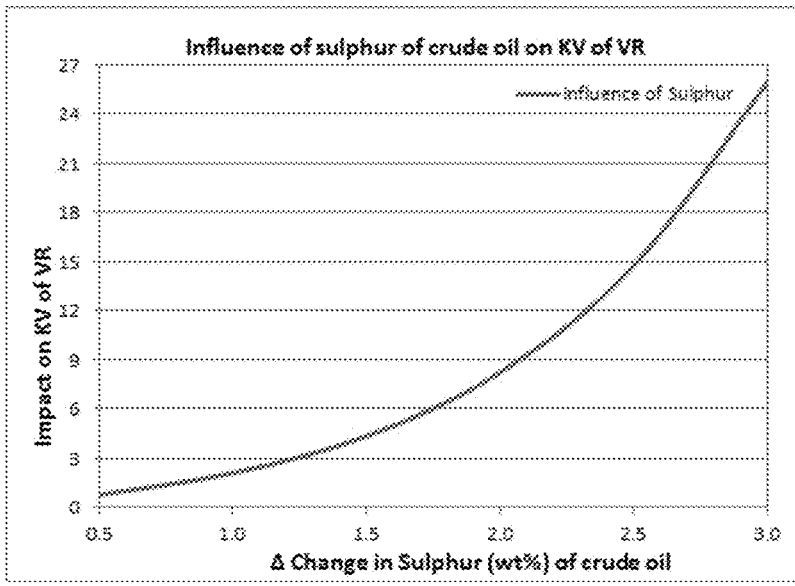
FIG. 6 illustrates impact on kinematic viscosity of vacuum residue of a crude oil due to change in sulphur content of crude oil, in accordance with an implementation of the present subject matter.

Further, on studying the influence of physical parameters of crude oil on kinematic viscosity of vacuum residue of the crude oil, it is observed that each parameter influences the kinematic viscosity on a different scale. For example, FIG. 6 illustrates the impact of change in Sulphur content in crude oil on the kinematic viscosity of vacuum residue of the crude oil. For given crude oil, a change of 0.5 units of Sulphur content influences the kinematic viscosity of vacuum residue substantially. The Sulphur content in crude oils may be measured using industrial protocol methods like ASTM D2622, D4294, and D5453.

Figure 7:
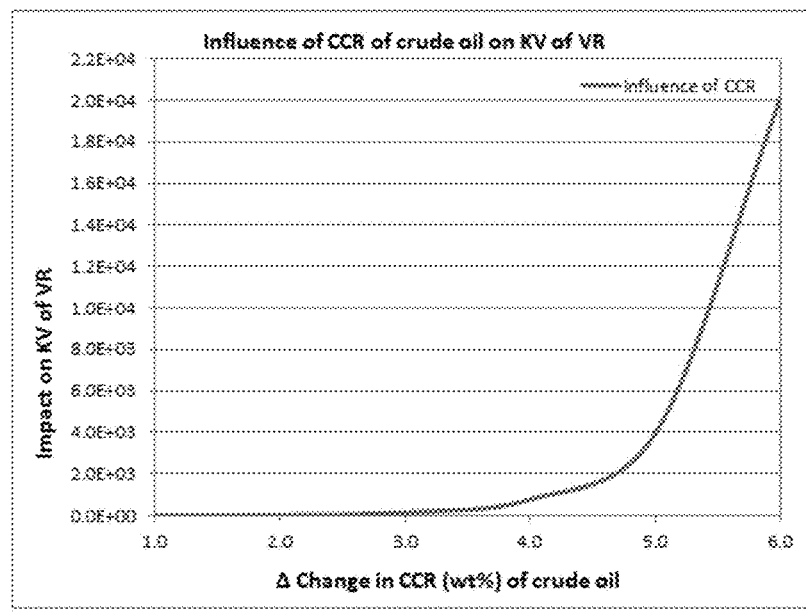
FIG. 7 illustrates impact on kinematic viscosity of vacuum residue of a crude oil due to change in CCR content of crude oil, in accordance with an implementation of the present subject matter.
Figure 8:
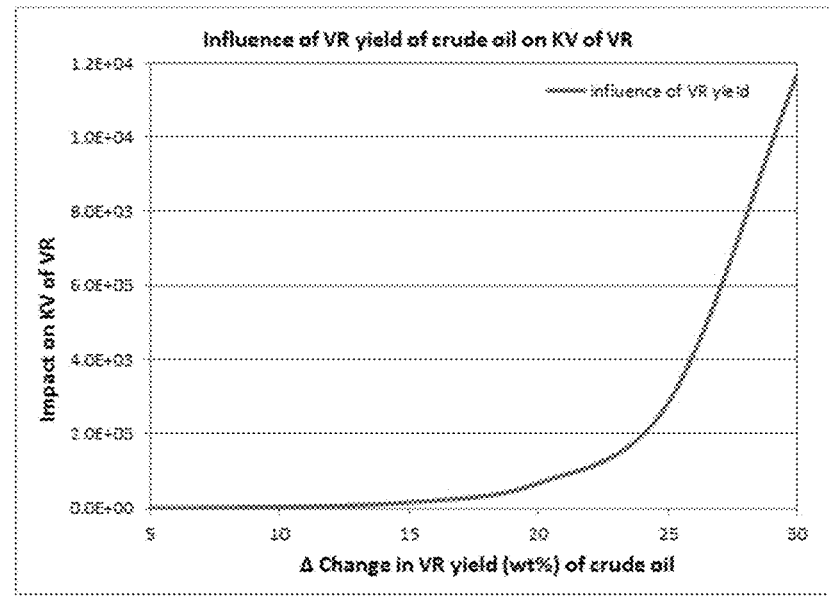
FIG. 8 illustrates impact on kinematic viscosity of vacuum residue of a crude oil due to change in vacuum residue yield of crude oil, in accordance with an implementation of the present subject matter.

FIG. 7 and FIG. 8 illustrate the impact on kinematic viscosity of vacuum residue due to change in Conradson Carbon Residue (CCR) content and change in Vacuum Residue yield, respectively.

The CCR content of crude oils may be measured using industrial methods like ASTM D189. When CCR content is changed in a crude oil, a very high influence on the value of kinematic viscosity of vacuum residue is observed. The relationship between the change in CCR content and its impact on kinematic viscosity of vacuum residue of crude oil may be represented by the graph as shown in FIG. 7. A 1 wt % of change in CCR content brings about a very high increase in kinematic viscosity and the kinematic viscosity of vacuum residue changes by a factor of 1000 when more than 3 wt % of CCR content is changed.

The Vacuum Residue yield of crude oil may be measured using industrial methods like TBP distillation (ASTM D2892) and Pot Still (D5236). The Vacuum Residue yield of crude oil has a high influence on kinematic viscosity of vacuum residue of the crude oil. The relationship between the change in Vacuum Residue yield and its impact on kinematic viscosity of vacuum residue of crude oil may be represented by the graph as shown in FIG. 8. As seen, 5 units of change in Vacuum Residue yield brings about a very high increase in kinematic viscosity and the kinematic viscosity of vacuum residue changes by a factor of 1000 when more than 10 units of Vacuum Residue yield is changed.

Thus it can be seen that the kinematic viscosity of vacuum residue of the crude oil is very sensitive to change in the CCR content and Vacuum Residue yield of the crude oil. For a given crude oil, the CCR content and Vacuum Residue yield may be changed up to 6 units and 30 units, respectively. In some examples, the change in CCR content and VR yield may be more than 6 units and 30 units respectively. Since different parameters may be varied to different extents in a crude oil, the API gravity of crude oil may be varied up to 30 units while CCR content and Vacuum Residue yield may be varied up to 6 units and 30 units, respectively.

Figure 9:
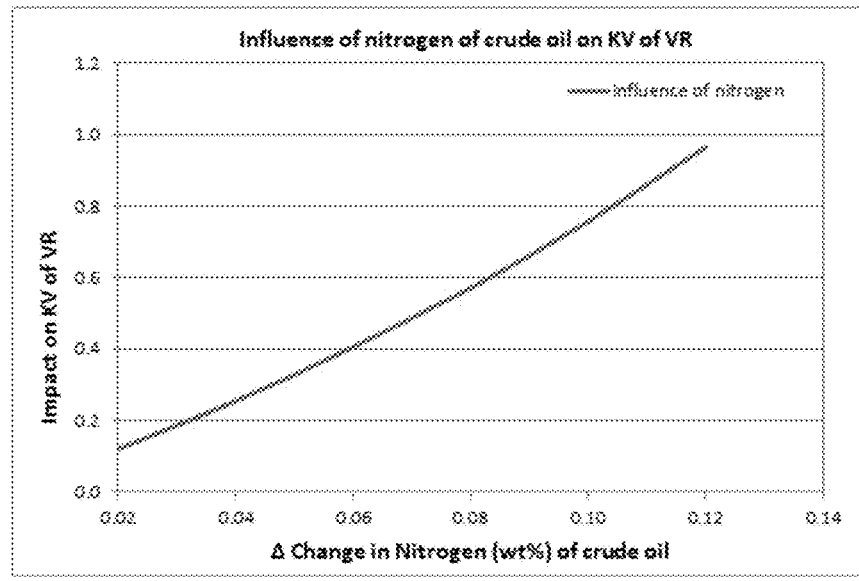
FIG. 9 illustrates impact on kinematic viscosity of vacuum residue of a crude oil due to change in nitrogen content of crude oil, in accordance with an implementation of the present subject matter.

FIG. 9 illustrates the impact on kinematic viscosity of vacuum residue of crude oil due to change in Nitrogen content in crude oil. It is measured using industrial protocol methods like ASTM D4629 and UOP 269. The Nitrogen content in a given crude oil is in trace amounts and hence the magnitude of change is much less in comparison to other parameters. Therefore, the change in Nitrogen content is in a scale of 0.1 units or less. The maximum change in kinematic viscosity of Vacuum Residue is a little less than 1 unit.

Figure 10:
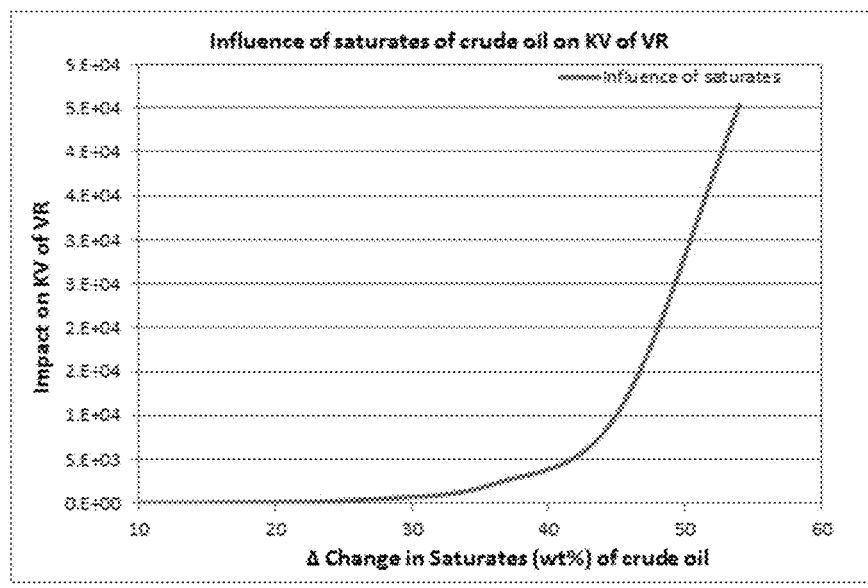
FIG. 10 illustrates impact on kinematic viscosity of vacuum residue of a crude oil due to change in saturates content of crude oil, in accordance with an implementation of the present subject matter.
Figure 11:
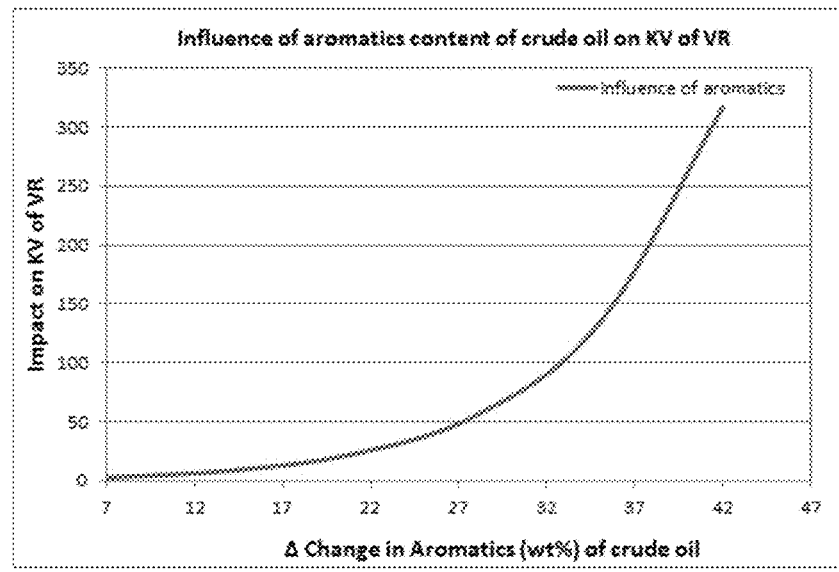
FIG. 11 illustrates impact on kinematic viscosity of vacuum residue of a crude oil due to change in aromatics content of crude oil, in accordance with an implementation of the present subject matter.
Figure 12:
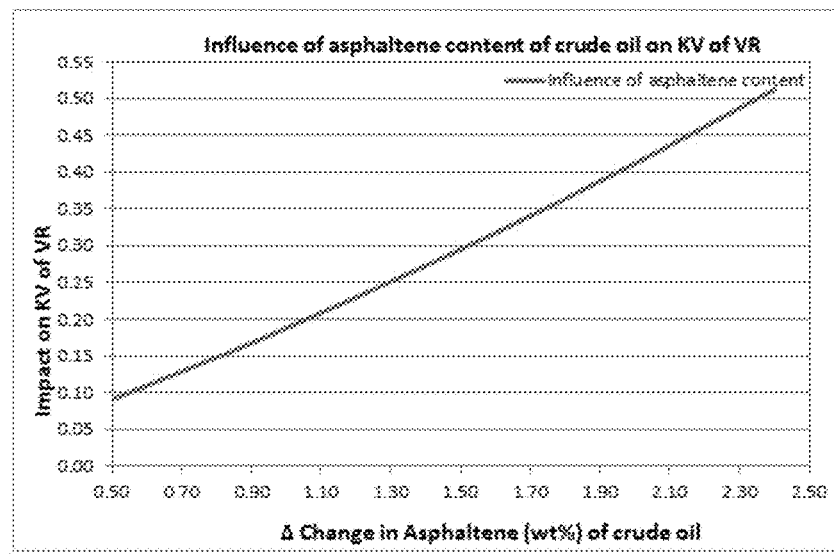
FIG. 12 illustrates impact on kinematic viscosity of vacuum residue of a crude oil due to change in asphaltene content of crude oil, in accordance with an implementation of the present subject matter.

FIG. 10, FIG. 11, and FIG. 12, illustrate the impact on kinematic viscosity of vacuum residue of crude oil due to change in saturates content, aromatics content, and asphaltene content in crude oil. Saturates, Aromatics, and Asphaltenes are three groups into which the components of heavy fraction of a petroleum fluid can be separated into. The chemical constitution of these contents is complex and the physical measurement and separation is difficult, in comparison to estimation of other physical parameters of crude oil.

Saturates content and Aromatics content may be determined by adsorption chromatography, typically from silica or silica/alumina. Saturates may be eluted with a paraffinic solvent, such as pentane or heptane, while Aromatics may be eluted either with paraffinic or moderately polar solvents, such as toluene. On elution of the contents, different measurement techniques can be used as known from the state of the art technology. Asphaltene aggregation, precipitation, or deposition can be predicted by modeling, filtration, or imaging methods. Further, it also can be measured using imaging methods or filtration and the asphaltene content may be measured by industrial protocol methods like ASTM D6560.

The change in saturates content in crude oil has a very high influence on the kinematic viscosity of vacuum residue, as per the measurements. A miniscule change of saturates content results in a change of more than 1000 units of kinematic viscosity of vacuum residue. For given crude oil, the saturates content may be varied from 10 to 55 units and the corresponding impact on kinematic viscosity may change from 0 to 104 units.

The aromatics content and asphaltene content of crude oil have comparatively less impact on kinematic viscosity of vacuum residue. For given crude oil, the measurements suggest that there is a maximum of 325 units of change in kinematic viscosity of vacuum residue due to change in aromatics content on crude oil. In case of the asphaltene content, there is a maximum of 0.50-0.55 units of change in kinematic viscosity of vacuum residue due to change in asphaltene content of crude oil.

The relationship of the physical parameters of crude oils and kinematic viscosity of vacuum residue of crude oil may be used for selection of physical parameters for generating coefficients of regression by regression analysis. The coefficients of regression may further be used for developing correlation models.

Based on the relationship between physical parameters of crude oil and kinematic viscosity of vacuum residue of crude oil as illustrated in FIG. 5-FIG. 12, appropriate physical parameters are chosen for developing correlation models. For example, physical parameters chosen for developing correlation models include at least one of Vacuum Residue yield and Conradson Carbon Residue (CCR) content. The Vacuum Residue yield and Conradson Carbon Residue (CCR) content has a high impact on the kinematic viscosity of vacuum residue of the crude oil as illustrated in FIG. 8 and FIG. 7. In addition, the measurement of Vacuum Residue yield and Conradson Carbon Residue (CCR) content is easier than that of saturates. In one implementation, at least one of Vacuum Residue yield and Conradson Carbon Residue (CCR) content along with any of other parameters including API gravity, Sulphur content, Nitrogen content, Saturates content, Aromatics content, Asphaltene content may also be used.

The physical parameters of a plurality of crude oils are used for developing the correlation models. The correlation models are then used for predicting kinematic viscosity of vacuum residue of an unknown crude oil. The physical parameters of the unknown crude oil are measured and used as inputs to the correlation model. The predicted kinematic viscosity of vacuum residue of crude is generated by the correlation model as the output.

FIG. 13-FIG. 17 illustrate scatter plots for validation between experimental kinematic viscosity of vacuum residue and kinematic viscosity of vacuum residue predicted using correlation models. Coefficients of correlation are obtained by performing regression analysis between the two quantities. The coefficients provide a measure of accuracy of prediction of kinematic viscosity of vacuum residue.

Figure 13:
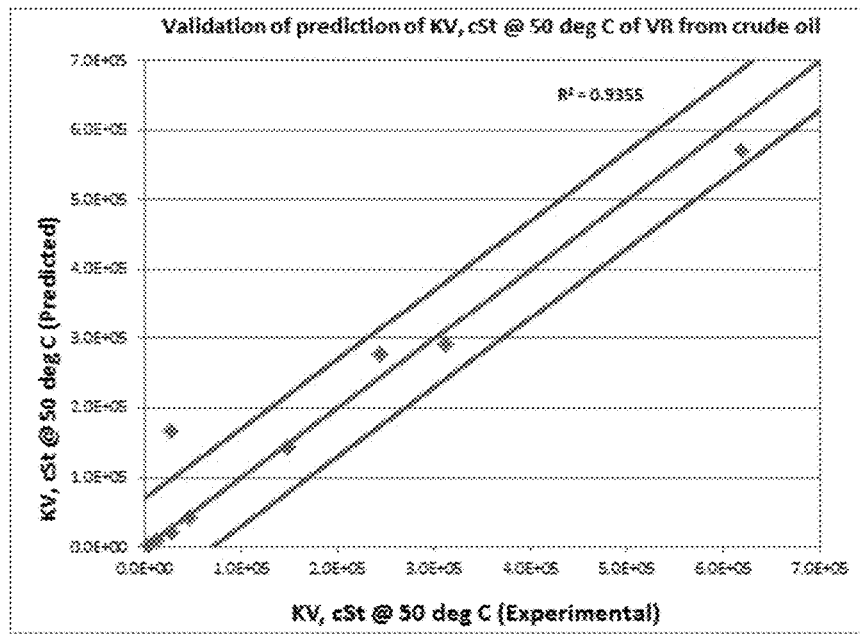
FIG. 13 illustrates a scatter plot between experimental values of KV-VR at 50 degree Celsius and KV-VR predicted at 50 degree Celsius from physical parameters of crude oil, in accordance with an implementation of the present subject matter.
Figure 14:
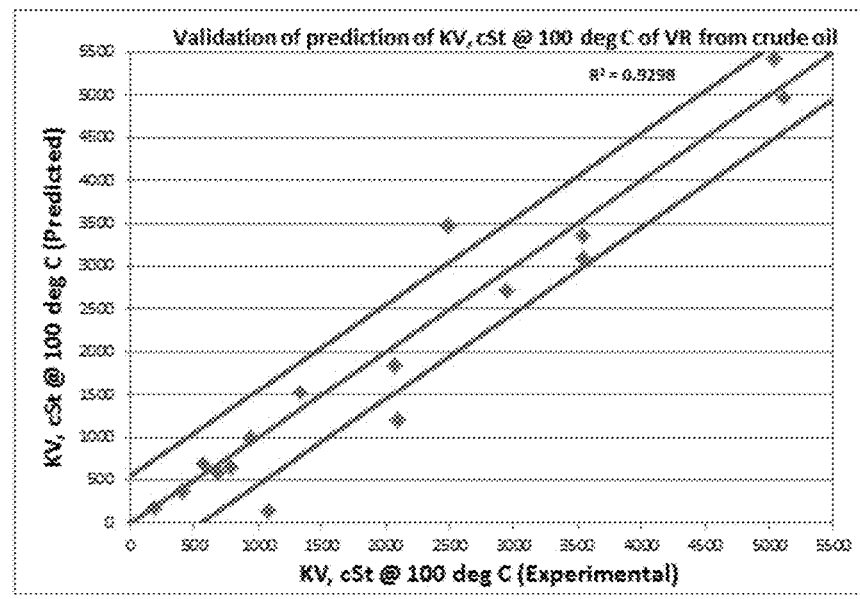
FIG. 14 illustrates a scatter plot between experimental values of KV-VR at 100 degree Celsius and KV-VR predicted at 100 degree Celsius from physical parameters of crude oil, in accordance with an implementation of the present subject matter.
Figure 15:
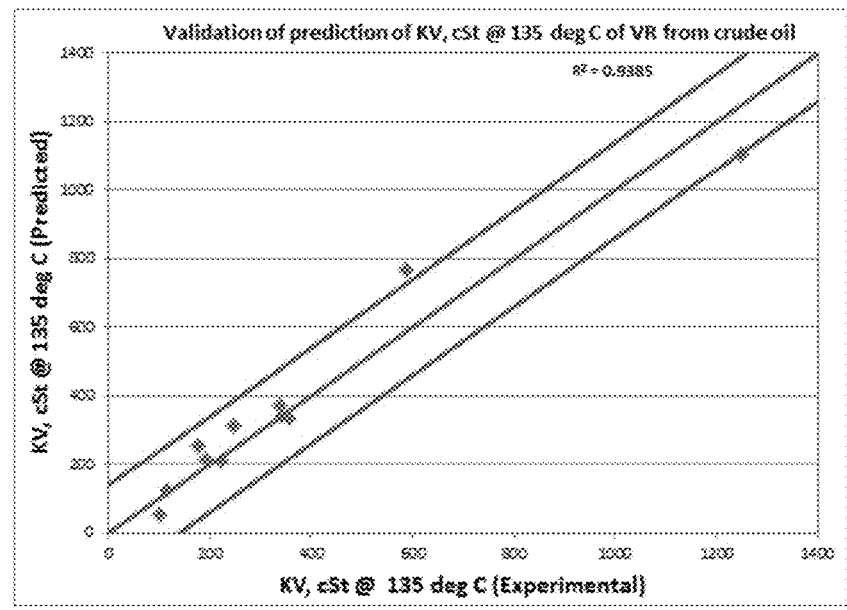
FIG. 15 illustrates a scatter plot between experimental values of KV-VR at 135 degree Celsius and KV-VR predicted at 135 degree Celsius from physical parameters of crude oil, in accordance with an implementation of the present subject matter.

FIG. 13, FIG. 14, and FIG. 15 depicts the regression analysis performed between the experimental values of kinematic viscosity and predicted values of kinematic viscosity at 50, 100, and 135 degree Celsius, respectively.

In these figures, the experimental values of kinematic viscosity of vacuum residue are derived from calculating kinematic viscosity from vacuum residue samples. The vacuum residue samples are combined with varying levels of cutter stocks and the corresponding values of kinematic viscosity of vacuum residue are measured. This methodology is illustrated in FIG. 4, wherein the kinematic viscosity of vacuum residue at 50 degree Celsius is measured for an amount of cutter stock ranging from 6-10%. Below 6% of cutter stock, the kinematic viscosity is so high due to which vacuum residue sample does not flow and kinematic viscosity cannot be measured by experimental means. The value of kinematic viscosity may be deduced by limiting the cutter stock value to 0 (zero) in the equation of the curve formed in the graph. On the other hand, the predicted values of kinematic viscosity of vacuum residue are be obtained by using correlation models. The first correlation model is used for predicting the kinematic viscosity of vacuum residue from physical parameters of the crude oil.

The coefficient of regression is calculated for each of the regression analyses performed for kinematic viscosity at 50, 100, and 135 degree Celsius. The coefficient of regression may be calculated by any well known method present in the state-of-the-art. The coefficients of correlation are calculated and equivalent to, R2=0.9355, at 50 degree Celsius;
R2=0.9298, at 100 degree Celsius;
R2=0.9385, at 135 degree Celsius.
where,
R2 denotes the coefficient of regression.

Figure 16:
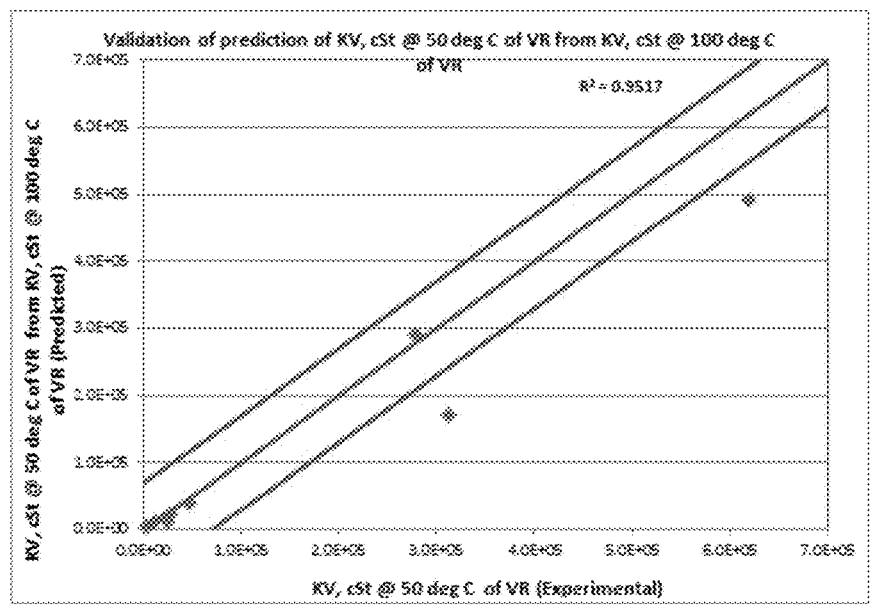
FIG. 16 illustrates a scatter plot between experimental values of KV-VR and KV-VR at 50 degree Celsius predicted from KV-VR at 100 degree Celsius, in accordance with an implementation of the present subject matter.
Figure 17:
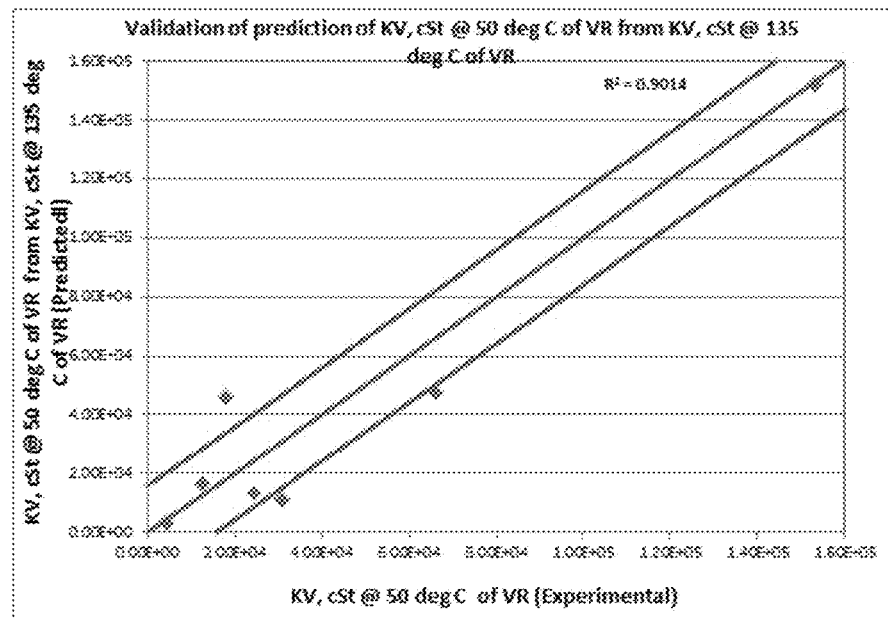
FIG. 17 illustrates a scatter plot between experimental values of KV-VR and KV-VR at 50 degree Celsius predicted from KV-VR at 135 degree Celsius, in accordance with an implementation of the present subject matter.

Similarly, the coefficients of correlation can be found out for second and third correlation models. FIG. 16 and FIG. 17 illustrate regression analysis between experimental values and predicted values of kinematic viscosity of vacuum residue based on the third correlation model. The third correlation model predicts kinematic viscosity of vacuum residue of the crude oil at 50 degree Celsius from kinematic viscosity of vacuum residue of the crude oil at 100 and 135 degree Celsius, respectively. The experimental values of kinematic viscosity may be obtained by measuring the values of kinematic viscosity of vacuum residue at 100 or 135 degree Celsius. The coefficient of regression is calculated as, R2=0.9355, KV-VR @ 50° C. from KV-VR @ 100° C.;

R2=0.9014, KV-VR @ 50° C. from KV-VR @ 135° C.

Figure 18:
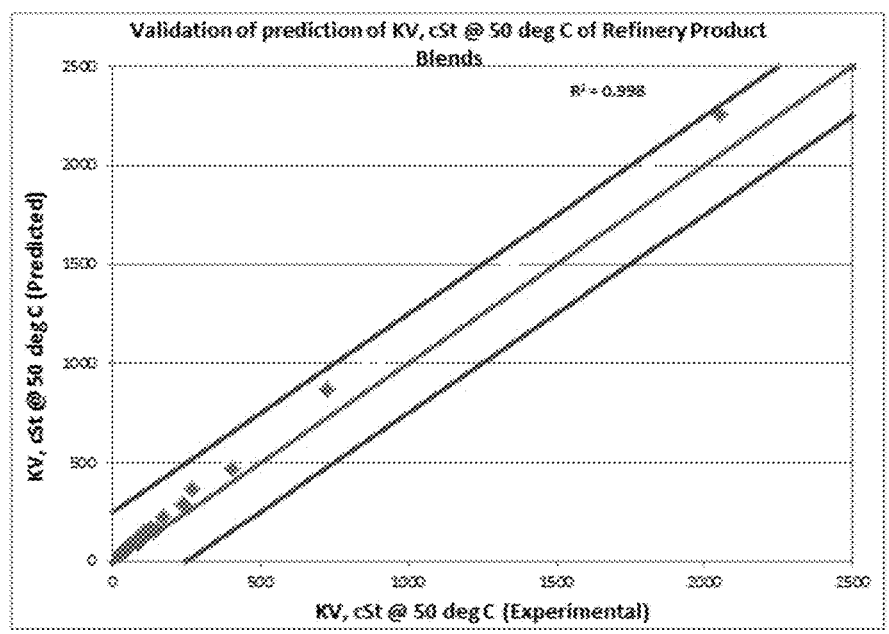
FIG. 18 illustrates a scatter plot between experimental values of KV of refinery product blends and KV of refinery product blends predicted from the kinematic viscosity of fractions of crude oils, in accordance with an implementation of the present subject matter.

FIG. 18 illustrates regression analysis between experimental values and predicted values of kinematic viscosity of refinery heavy product blends based on the second correlation model. The second correlation model predicts the kinematic viscosity of refinery heavy product blends from kinematic viscosity of fractions of crude oils derived from different or same crude oils or streams can be taken from other refinery processing units.

The coefficient of regression is calculated for each of the regression analyses by any well known method present in the state-of-the-art. The coefficients of correlation are calculated and equivalent to, $R^2$=0.998, kinematic viscosity of crude oil blend.
where,
$R^2$ denotes the coefficient of regression.

The values of R2 show good correlation between the experiment values and predicted values of kinematic viscosity. The present subject matter, in one embodiment, provides an accurate prediction of kinematic viscosity of vacuum residue at 50 degree Celsius. Another embodiment provides prediction of kinematic viscosity of refinery heavy product blends from fractions of crude oils derived from different or same crude oils. The prediction of kinematic viscosity is very accurate, as illustrated in the figures.

The predicted kinematic viscosity of vacuum residue at 50 degree Celsius may be used for estimating an amount of the cutter stock required in crude oil processing. Therefore, the accurate prediction of kinematic viscosity from correlation models can prevent use of excess cutter stock, thereby minimizing cutter stock wastage and unnecessary costs.

Although implementations for prediction of kinematic viscosity of vacuum residue of crude oil have been described in language specific to structural features and/or methods, it is to be understood that the appended claims are not necessarily limited to the specific features or methods described. Rather, the specific features and methods are disclosed as exemplary implementations for prediction of refining characteristics of oil.

All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for predicting kinematic viscosity of a fraction of a crude oil to optimize selection of crude oils, the fraction comprising vacuum residue, the method comprising:
   receiving, by a processor, physical parameters of the crude oil as an input, wherein the physical parameters comprise Vacuum Residue yield and Conradson Carbon Residue (CCR) content;
   determining, by the processor, kinematic viscosity of the fraction of the crude oil at a first predetermined temperature, wherein the kinematic viscosity of the fraction is determined at the first predetermined temperature based on a first correlation model generated based on the physical parameters of known crude oil samples and the kinematic viscosity at the first predetermined temperature of the fraction obtained from each of the known crude oil samples, wherein when the first predetermined temperature is less than a flow point of the fraction, the kinematic viscosity of the fraction obtained from each of the known crude oil samples is determined by:
      adding different amounts of cutter stock to the fraction obtained from each of the known crude oil samples to obtain flowable mixtures of the cutter stock and the fraction;
      determining the kinematic viscosities of the flowable mixtures to obtain a trend in change in kinematic viscosity with amount of cutter stock added; and
      extrapolating, from the trend, the kinematic viscosity of the fraction with no cutter stock added; and
   generating an output based on the first correlation model corresponding to the input, wherein the output is the kinematic viscosity of the fraction of the crude oil at the first predetermined temperature to optimize the selection of crude oils for refinery processing.

2. The method as claimed in claim 1, wherein the method comprises determining the kinematic viscosity of a heavy product blend from the kinematic viscosity of each fraction of the heavy product blend based on a second correlation model, wherein the heavy product blend includes at least the fraction comprising vacuum residue.

3. The method as claimed in claim 2, wherein the heavy product blend corresponds to a blend of different fractions of the crude oil derived from different or same crude oils.

4. The method as claimed in claim 1, wherein the method comprises determining kinematic viscosity of the fraction of the crude oil at a second predetermined temperature from the kinematic viscosity of the fraction of crude oil at the first predetermined temperature based on a third correlation model.

5. The method as claimed in claim 1, wherein the physical parameters include one or more of API gravity, Sulphur content, Hydrogen content, Nitrogen content, Mercaptan value, Pour point, Saturates, Aromatics, Resins and Asphaltenes.

6. The method as claimed in claim 1, wherein the kinematic viscosity of the fraction of crude oil generated determines production requirements of Fuel oil, Low Sulphur Heavy Stock, Low Sulphur Fuel Oil, and bitumen.

7. The method as claimed in claim 1, wherein the first predetermined temperature is in a range of 50 degree Celsius to 135 degree Celsius.

8. The method as claimed in claim 1 further comprising:
   calculating, by the processor, the amount of cutter stock for crude oil processing based on the determined kinematic viscosity of the fraction comprising vacuum residue.

9. The method as claimed in claim 8, wherein the cutter stock is a blend of one or more fractions of the crude oil.

10. The method as claimed in claim 8, wherein the cutter stock includes one or more of kerosene, gasoline, jet fuel, diesel, Naphtha, VGO, CLO, LCO, LSHS, FO, LSFO, and VR.

11. The method as claimed in claim 8, wherein the amount of cutter stock is calculated as a weight percentage of a refinery product.

12. The method as claimed in claim 8, wherein the crude oil processing includes optimal evacuation of vacuum residue from a vacuum distillation column.

13. A system for predicting kinematic viscosity at a predetermined temperature, the system comprising:
   a processor;
   a database comprising crude oil data, wherein the crude oil data comprises physical parameters of a crude oil;
   a memory coupled to the processor and the database, the memory comprising;
   a first prediction module to predict kinematic viscosity of a fraction of the crude oil at the predetermined temperature from the physical parameters of the crude oil based on a first correlation model, the fraction of the crude oil comprising vacuum residue, wherein the physical parameters of the crude oil include vacuum residue yield and Conradson Carbon Residue (CCR) content, wherein the first correlation model is generated at the first predetermined temperature based on the physical parameters of known crude oil samples and the kinematic viscosity of the fraction obtained from each of the known crude oil samples, wherein when the first predetermined temperature is less than a flow point of the fraction, the kinematic viscosity of the fraction obtained from each of the known crude oil samples is determined by:
      adding different amounts of cutter stock to the fraction obtained from each of the known crude oil samples to obtain flowable mixtures;
      determining the kinematic viscosities of the flowable mixtures to obtain a trend in change in kinematic viscosity with amount of cutter stock added to the fraction; and
      extrapolating the kinematic viscosity of the fraction with no cutter stock added from the trend; and
   a second prediction module to predict the kinematic viscosity of a heavy product blend from the kinematic viscosity of fractions of the heavy product blend.

14. The system as claimed in claim 13, wherein the memory comprises a third prediction module to predict the kinematic viscosity of the fraction of crude oil at a second predetermined temperature from the kinematic viscosity of the fraction at the predetermined temperature.

15. The system as claimed in claim 13, wherein the predetermined temperature is in a range of 50 degree Celsius to 135 degree Celsius.

16. The system as claimed in claim 13, wherein the memory comprises a fourth prediction module to predict the amount of optimal cutter stock requirement for evacuating vacuum residue on processing of the crude oil based on the determined kinematic viscosity of the fraction comprising vacuum residue.

17. The system as claimed in claim 13, wherein the physical properties include one or more of API gravity, Sulphur content, Hydrogen content, Nitrogen content, Mercaptan value, Pour point, Saturates, Aromatics, Resins and Asphaltenes.

18. The system as claimed in claim 13, wherein the heavy product blend is obtained by blending different fractions of the crude oils derived from different or same crude oils.

\* \* \* \* \*